Oct. 18, 1949. C. D. CORLISS Plant Pat. 881
EUONYMUS FORTUNEI PLANT
Filed Dec. 19, 1947
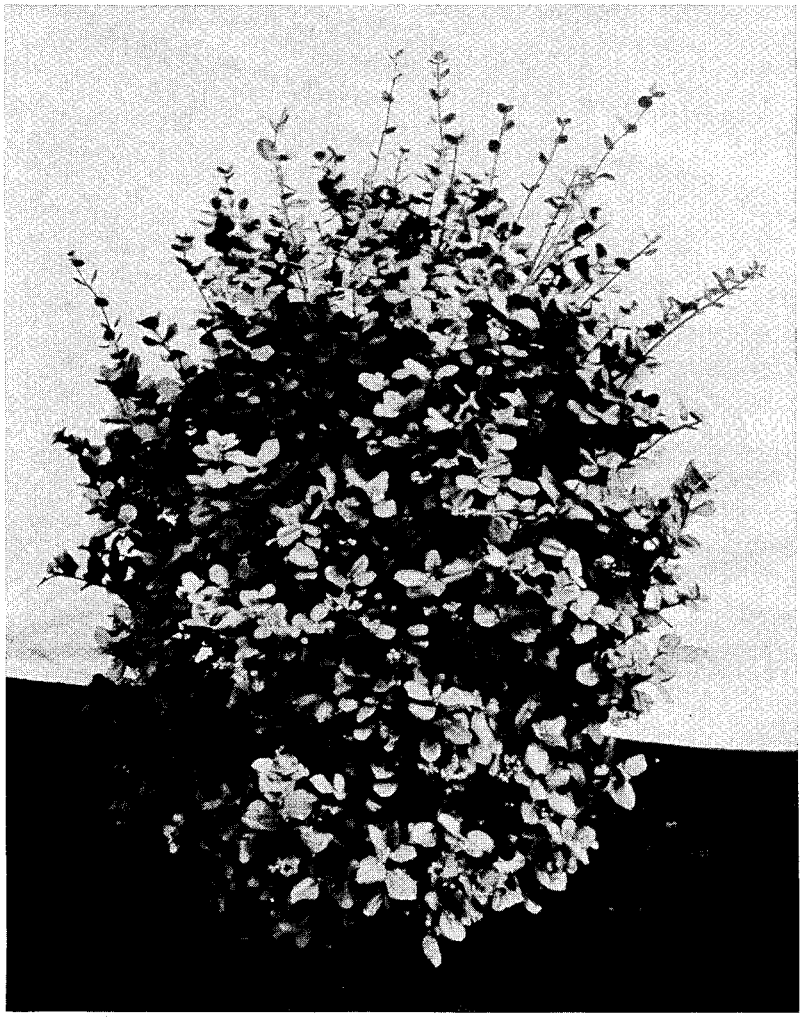
Inventor
C. D. Corliss
By Robb & Robb
Attorneys Patented Oct. 18, 1949

Plant Pat. 881

UNITED STATES PATENT OFFICE

881

EUONYMUS FORTUNEI PLANT

Clifford D. Corliss, Magnolia, Mass., assignor to Corliss Bros. Inc., Gloucester, Mass., a corporation of Massachusetts Application December 19, 1947, Serial No. 792,707

1 Claim. (Cl. 47—59)

This invention relates to a new and distinct variety of *Euonymus fortunei* plant, an evergreen originated by me from a selected seedling produced by crossing *Euonymus fortunei* vegeta and *Euonymus fortunei* radicans.

This new variety possesses a number of desirable characteristics clearly distinguishing it from its parents and other similar evergreen varieties, and the following comparisons will suffice to point out its particular advantages of utility for ornamental purposes.

It is well known that *Euonymus fortunei* varieties of vegeta and radicans embody irregular and prostrate plants of viney growth that grow upright only if supported. The habit of my new shrub is distinctly upright without support, the whole plant growing and branching compactly from one central stem, and the branches and branchlets being almost perfectly uniform. The ordinary vegeta type can be trained to shrub form only by constant shearing, whereas my new variety requires no shearing, and in fact it has never been sheared. It is well known that neither the radicans variety nor the vegeta variety can be grown or trained for hedging unless sheared and supported. The variety of the present invention can be used as an excellent hedge plant because of its upright growth entirely unsupported. It is definitely not a vine in any way, shape or manner.

The plant of this new variety is an evergreen shrub possessing great decorative value in its distinctive bushy erect habit of growth, in its sturdy character and appearance, its beautiful clusters of berries in the fall, and its formation of a neat, compact, uniform shrub with an average height of 4–5 feet, and spread of about 2½ feet. Like vegeta, this shrub of mine bears, very heavily, clusters of the bittersweet type berries. These berries, seven to ten in a cluster, when ripened to expose their bright orange coloring enhance the beauty of the shrub.

The growth of the plant is likewise unique and advantageous for use as a specimen shrub plant where formal effects are desired. This is due to the fact of the uniformity and compactness with which the plant grows from one central stem with erectness of the lateral branches and branchlets affording the comparative uniformity of shape, previously mentioned.

My Euonymus plant presents the appearance of a deeper green colored foliage as distinguished from the appearance of the dark green coloring of the vegeta variety which it resembles in leaf character because of its thicker leaves. The leaves of my evergreen Euonymus are somewhat broader and more ovate than vegeta, as well as having a glossy appearance as distinguished from the dull leaf of vegeta.

In addition to the foregoing advantages, my evergreen Euonymus apparently is not susceptible to scale, or other diseases, since nothing has affected or attacked it up to the present time. Another very important feature is its hardiness, having withstood as low as 20 degrees below zero with no ill effects, on the North Shore of Massachusetts, and no sign of any winter burn which is more or less prevalent in the vegeta type. My plant stands extremely dry conditions well.

The strong fibrous root system of my new evergreen Euonymus permits easy and successful transplanting of the shrub with a good ball of earth. These plants do well in average garden soil which greatly widens the scope of their use.

Asexual reproductions by cuttings of this new variety were made at Ipswich, Mass., and they show the foregoing characteristics come true to form and are established.

The accompanying drawing illustrates a specimen of this new variety, depicting its habit of erect uniformly branched growth.

The following is a detailed description of the new variety, color terminology being in accordance with ordinary dictionary significance:

Classification: *Euonymus fortunei* var. (vegeta × radicans).

Habit: Distinctly upright without support; plant arises from a central stem; form of shrub ovoid, well bushed at the base. The regular vegeta which it resembles in leaf character is a more or less prostrate vine which grows upright only if supported.

Leaves and branchlets: Leaves evergreen, 3–5 cm. long, opposite, petioled, broad ovate to suborbicular; margin crenate-serrate; apex emarginate; dark glossy green above; light dull green beneath; veins slightly more prominent on the upper than on the under surface; texture somewhat thicker than on regular vegetus. *Branchlets*—medium green, minutely warty, tending to form aerial rootlets on the older branches. Buds elongated, pointed, budscales imbricated, lighter color than the branchlets.

Flowers: In axillary cymes, four to five parted, inconspicuous.

Fruit: Sub-globose, lobed, 3 to 5 celled capsules with irregularly placed spiny protuberances, 7 to 10 capsules to a cluster; capsule cream-colored with a pinkish tinge, opening loculicidal to expose one or two seeds in each cell, each seed covered with a bright orange aril; seeds white.

I claim:

A new and distinct horticultural variety of *Euonymus fortunei* plant herein shown and described and characterized particularly by its erectness and shapeliness of shrub growth in the absence of support; its vigorous, sturdy and bushy habit of growth in forming from one central stem, a neatly rounded evergreen bush; its large, thick and glossy leaves; its hardiness and resistance to diseases; ability to stand dry conditions, and the absence of any showing of winter burn.

CLIFFORD D. CORLISS.

No references cited.